United States Patent
Lovoi et al.

(10) Patent No.: US 7,127,033 B2
(45) Date of Patent: Oct. 24, 2006

(54) MINIATURE X-RAY TUBE COOLING SYSTEM

(75) Inventors: Paul A. Lovoi, Saratoga, CA (US); John Rieke, Mercer Island, WA (US); Alex Lim, Santa Clara, CA (US); Peter C. Smith, Half Moon Bay, CA (US); Thomas W. Rusch, Hopkins, MN (US)

(73) Assignee: Xoft, Inc., Fremont, CA (US)

( * ) Notice: Subject to any disclaimer, the term of this patent is extended or adjusted under 35 U.S.C. 154(b) by 0 days.

(21) Appl. No.: 10/789,653

(22) Filed: Feb. 28, 2004

(65) Prior Publication Data

US 2006/0171506 A1    Aug. 3, 2006

(51) Int. Cl.
*H01J 35/32* (2006.01)

(52) U.S. Cl. .................. 378/130; 378/199; 378/200

(58) Field of Classification Search ............... 378/119, 378/121, 122, 141, 199, 200, 130; 600/2, 600/433, 435
See application file for complete search history.

(56) References Cited

U.S. PATENT DOCUMENTS

| | | | |
|---|---|---|---|
| RE34,421 E * | 10/1993 | Parker et al. ............... 378/121 |
| 5,621,780 A | 4/1997 | Smith et al. ................. 378/65 |
| 5,854,833 A | 12/1998 | Hogan et al. ........... 379/114.14 |
| 6,319,188 B1 | 11/2001 | Lovoi ............................. 600/3 |
| 6,390,967 B1 * | 5/2002 | Forman et al. ................ 600/3 |
| 2004/0087827 A1 | 5/2004 | Lubock |
| 2004/0218724 A1 * | 11/2004 | Chornenky et al. ......... 378/141 |

* cited by examiner

*Primary Examiner*—Courtney Thomas
(74) *Attorney, Agent, or Firm*—Thomas M. Freiburger

(57) ABSTRACT

A miniature x-ray tube is cooled using a catheter preferably having multiple small lumens for inflow and outflow of coolant. Inflow may be through an outer lumen(s) in a concentric-extrusion catheter, the liquid turning back at the distal end of the catheter to a proximal flow over the anode end of the x-ray tube and through an inner lumen within which the x-ray tube is positioned. A coolant distribution head may engage with the anode end of the x-ray tube, with small orifices so as to distribute coolant essentially evenly over the anode surface. Temperature and flow rate of the inflowing coolant liquid are balanced so as to optimize heat transfer while efficiently carrying coolant through small lumens without the need for high pressures. Some embodiments use the inflation liquid in an applicator balloon as the coolant, with the liquid actively flowing or, in a simplified system, with the liquid static.

45 Claims, 7 Drawing Sheets

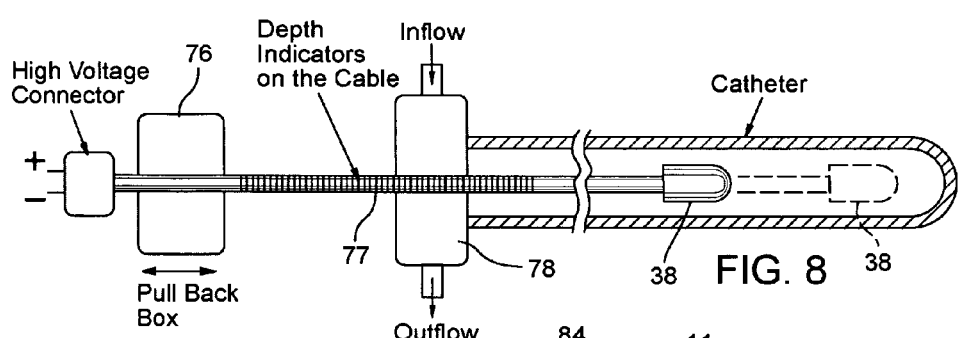
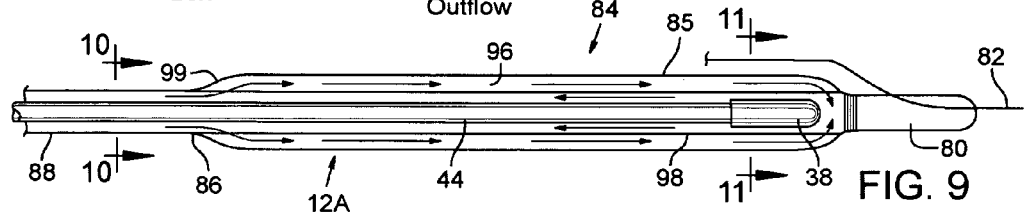
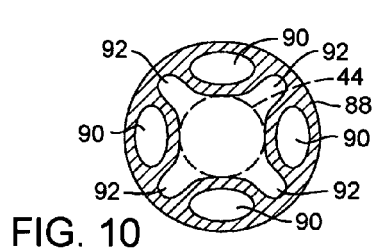 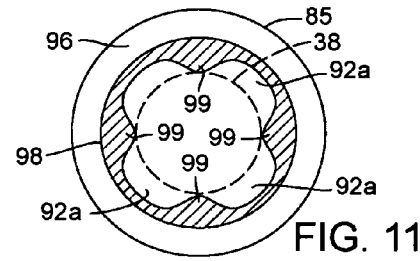

MINIATURE X-RAY TUBE COOLING SYSTEM

BACKGROUND OF THE INVENTION

The invention concerns miniature x-ray tubes for therapeutic treatment of specific areas within the human body, such as a blood vessel, duct or other small lumen, and in particular the invention concerns cooling of such a miniature x-ray tube in an efficient manner without requiring an unduly large catheter to carry the coolant.

Miniature or small x-ray tubes for human therapeutic treatment are discussed in several prior patents, including U.S. Pat. Nos. 5,854,822, 5,621,780 and 6,319,188. Such small x-ray tubes have been intended for treatment of tumors within surgical openings in the body, for treatment within blood vessels using a catheter containing the tube, and for other radiation treatments within the body. Cooling of miniature x-ray tubes, particularly when used within lumens of the body, is an important issue. One prior approach has been an open loop cooling system, wherein a liquid coolant (saline solution) is dumped into the blood flow after flowing over the anode end of an x-ray tube. With such an open system heated saline solution can damage blood cells if heated beyond 43° C. Moreover, excessive flow of saline into the blood can be deleterious. Still further, an open loop system requires extra protective measures to assure sterility of the coolant liquid.

In other x-ray tube cooling arrangements, the blood itself has been used as a coolant. This is particularly risky because when the blood directly contacts the hot anode (or a structure directly in contact with the anode), the blood is almost certain to be overheated and to experience cell damage and cause thrombus to form.

There is a need for a miniature x-ray tube cooling system, particularly a closed loop cooling system, which effectively, reliably and efficiently cools a miniature x-ray tube without requiring an objectionable expansion of the size of the catheter carrying the tube.

SUMMARY OF THE INVENTION

The present invention provides such a cooling system, as part of a catheter within which the x-ray tube is inserted into a lumen of the body such as a blood vessel or duct.

A miniature x-ray tube, which may be small enough to enter blood vessels and other small lumens of the human body, is cooled using a catheter having multiple small lumens for inflow and outflow of coolant liquid. Preferably the inflow of coolant liquid is through an outer lumen or lumens in a concentric-extrusion catheter, the liquid turning back at the distal end of the catheter to a proximal flow direction to flow over the anode end of the x-ray tube and through an inner lumen within which the x-ray tube and its attached flexible cable are positioned.

In one preferred form the catheter has a coolant distribution head which engages with the anode end of the x-ray tube and has a series of small orifices in a wall distal to the anode so as to distribute the coolant liquid essentially evenly over the surface of the anode. The outer annulus of space between the inner and outer extrusions is divided into multiple inflow lumens so that if the catheter passes through a sharp bend and collapses one lumen, other lumens still carry the coolant liquid. The coolant liquid preferably is degassed and may include a surfactant, for improving heat transfer and reducing surface tension.

The temperature of the inflowing coolant liquid, and its volumetric flow rate, are balanced so as to optimize heat transfer while efficiently carrying the coolant through very small lumens without the need for very high pressures. In a preferred embodiment the outer extrusion of the catheter is of a low thermally conductive material, thus insulating and minimizing heating of the coolant as it flows toward the x-ray tube.

Other cooling embodiments are useful for certain applications, using static cooling from the liquid used to inflate an applicator balloon, or flowing applicator inflation liquid. These embodiments can reduce x-ray catheter cost and complexity as well as improving cooling.

The liquid that fills and expands an applicator balloon is used to cool the x-ray source. The saline or other fluid can be static, or flowing with pressure control to maintain the proper expansion of the balloon. In an application in which a relatively large volume of liquid fills the applicator and in which treatment time is relatively short, static fills of liquid can be adequate to cool the x-ray source. This works well as long as the fluid does not heat beyond allowable temperatures. Convection can be used to circulate the fluid over the x-ray source.

A modification to the static approach includes a heat exchanger built into the applicator balloon to allow for heat exchange and heat removal using a moving liquid that does not come into contact with either the x-ray source or the applicator inflation liquid.

In a nonstatic embodiment, the balloon inflation liquid still is used for cooling, but it is pumped into the applicator balloon and removed while maintaining a differential pressure sufficient to maintain the expansion of the applicator balloon.

It is therefore among the objects of this invention to improve over previously described cooling arrangements for miniature x-ray tubes, by providing a closed loop cooling system which uses very small channels or lumens within a catheter, maintaining the catheter diameter very small, with efficient features for assuring even distribution of coolant over the anode and over the x-ray tube, for optimizing heat transfer and for monitoring to assure continued flow of coolant during a procedure; and by providing static cooling systems as an alternative for certain applications. These and other objects, advantages and features of the invention will be apparent from the following description of a preferred embodiment, considered along with the accompanying drawings.

DESCRIPTION OF THE DRAWINGS

FIG. 8 is a system schematic view showing a specific embodiment of the cooling system of the invention.

FIG. 9 is a longitudinal section view schematically showing the distal end of the catheter in one preferred and specific embodiment.

FIG. 10 is a transverse sectional view showing an embodiment of an extrusion for the catheter, with inflow and outflow lumens for coolant liquid, proximal of the radiation source/applicator itself.

FIG. 11 is a transverse section showing another extrusion providing for inflow and outflow of coolant liquid, in the area of the radiation source/applicator.

DESCRIPTION OF PREFERRED EMBODIMENTS

Figure 1:
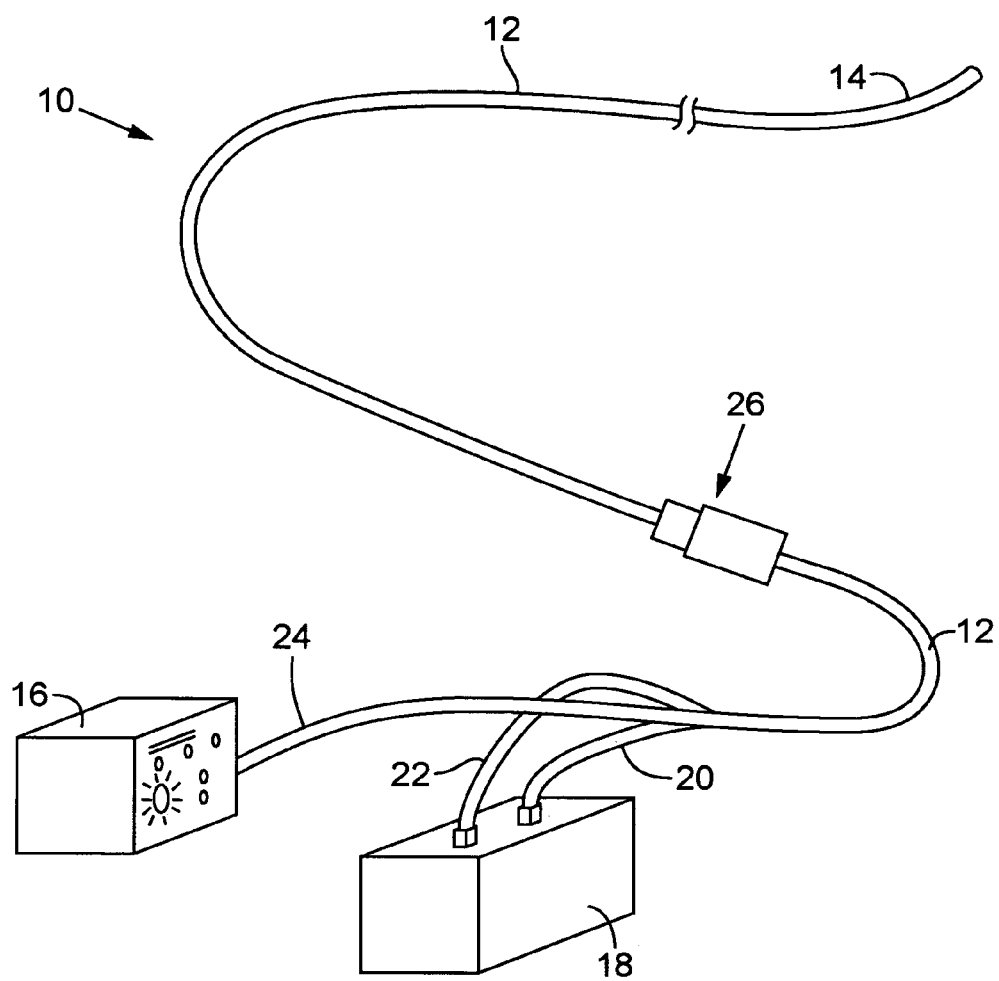
FIG. 1 is a schematic view showing a system according to the invention.

In the drawings, FIG. 1 shows a system 10 for administering x-ray treatment within a body cavity, channel or lumen via a catheter 12 having a distal end 14 containing a miniature, switchable x-ray tube, and including a controller 16 for the x-ray tube. The catheter 12 in a preferred embodiment is of small enough diameter to be used in blood vessels, mammary ducts and other small lumens of the body, and may have an external diameter on the order of about 0.5 mm to 4 mm. The apparatus 10 includes a cooling system for cooling the x-ray tube as it emits radiation within the body, including a coolant liquid reservoir 18 with a pump and other features described below. As indicated, coolant inflow and outflow or return tubes 20 and 22 connect to the reservoir 18 and into a portion of the catheter 12 near the proximal end 24. The high voltage cable from the controller 16 extends through the entire catheter 12, preferably joined by the coolant inflow and outflow 20, 22 at a position spaced from the controller 16, as shown. Preferably a coupler is included at 26, enabling separation of most of the length of the catheter 12 from the proximal end portion for purposes of sterilization and replacement of the active portion of the catheter that enters the body.

Figure 2:
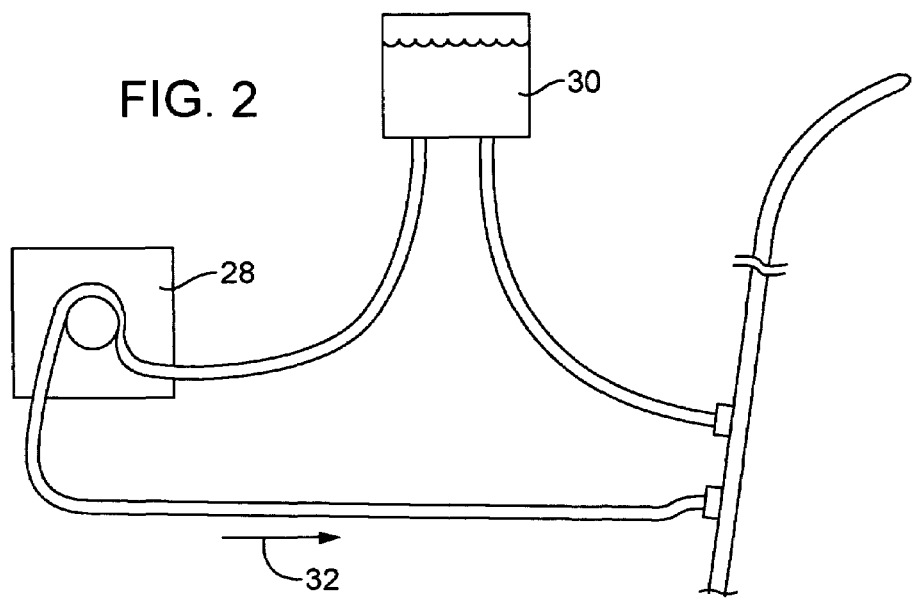
FIG. 2 is a simple a schematic view indicating a cooling liquid circulation scheme in one embodiment of the invention.

FIG. 2 schematically indicates use of a peristaltic pump 28 in the cooling system of the invention. In this case the reservoir 18 shown in FIG. 1 would be replaced in part by the components shown. A reservoir is provided by a coolant liquid-filled bag 30, and the peristaltic pump 28 advances the coolant liquid in the usual way, without contact of any pump parts with the liquid itself, preventing contamination. Flow is in the direction of the arrow 32. The coolant is thus pumped into the inflow lumen of the x-ray catheter with a positive pressure.

Figure 3:
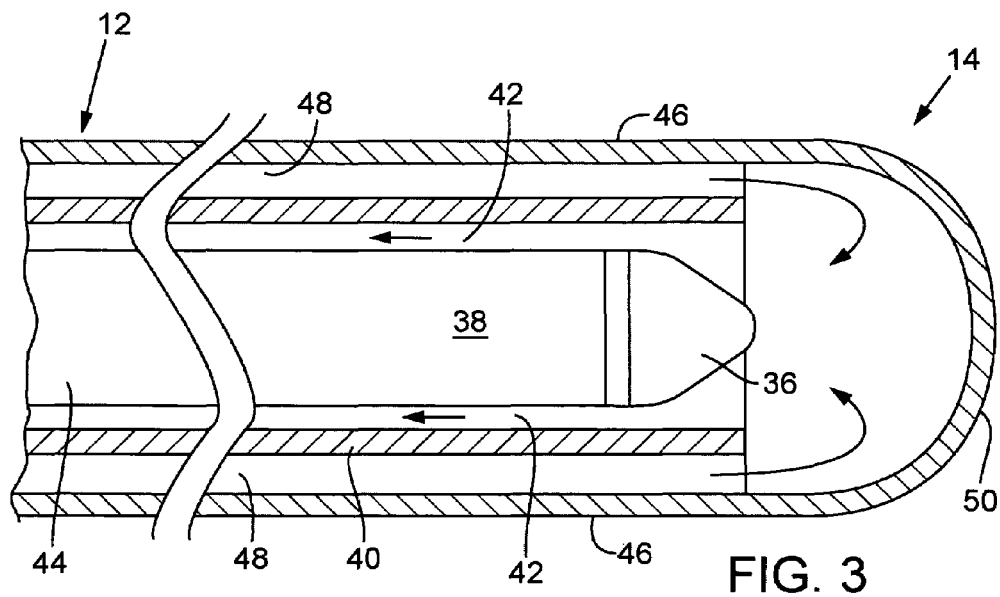
FIG. 3 is a schematic view in longitudinal section showing a distal end of a catheter of the apparatus of the invention and is indicating a preferred coolant circulation arrangement.

FIG. 3 shows in cross section the distal end 14 of the catheter. The drawing reveals schematically the anode end 36 of an x-ray tube 38 within. The tube 38 is located within the internal space defined by an inner tube or duct 40 in this preferred form of cooling arrangement. This leaves an annular liquid flow space 42 surrounding the x-ray tube 38, and, in the length of the catheter 12 proximal of the x-ray tube, surrounding a cable 44 leading back to the controller 16 shown in FIG. 1.

In this embodiment, an outer tube 46 of the catheter surrounds the inner tube 40 as shown, leaving another annular flow space 48. The distal end 50 of the outer tube 46 is closed as shown, and in this cooling arrangement the coolant liquid flows in the inflow direction through the outer annular lumen or lumens 48, changes direction at the dead end of the outer tube 46 and returns back toward the proximal direction over the anode 36 and through the inner and the annular lumen 42 to return to the coolant reservoir.

Also in this form of the system of the invention, the outer duct or tube 46 is formed of low thermal conductivity material. Since the coolant liquid flows through the outer annular lumen 48 en route to the anode, and this liquid must be cooler than the anode, and preferably cooler than the body temperature, insulation is important in this outer tube.

The anode end 36 of the x-ray tube is advantageously dome shaped or generally conical or bullet shaped as shown for better flow and distribution of the coolant liquid over the anode. These shapes are also discussed in the co-pending application Ser. No. 10/371,401, filed Feb. 21, 2003, assigned to the assignee of the present invention. The co-pending application also describes several exterior anode end surface shapes for helping to distribute the coolant liquid fully over the surface of the anode end for efficient cooling.

Figure 4:
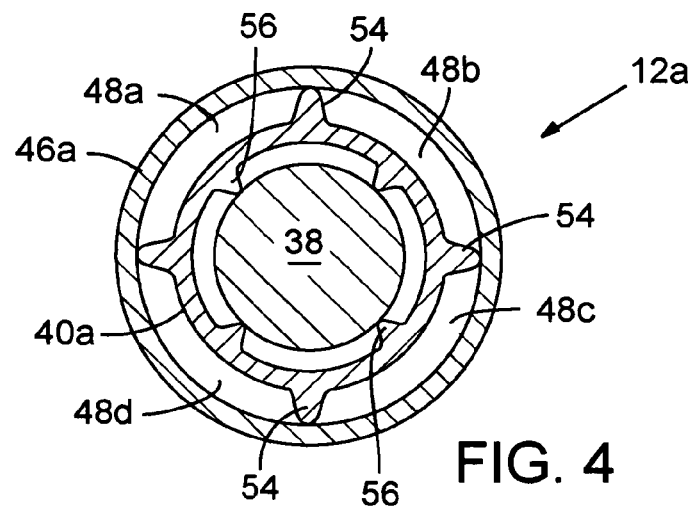
FIG. 4 is a transverse cross sectional view showing inflow and outflow or return coolant liquid flow channels as formed between two coaxial extrusions.

FIG. 4 shows in cross section a catheter 12*a* with a preferred tube structure for providing multiple lumens in both inflow and outflow directions. In this form of catheter structure, the outer tube 46*a* and inner tube 40*a*, both extrusions, are fitted closely together to define, dividing the annular space between the two extrusions into 48*a*, 48*b*, 48*c* and 48*d*. In the form shown, the outer extrusion 46*a* is formed essentially as a simple cylinder, while the inner extrusion 40*a* has ridges 54 on its exterior which, when the inner extrusion 40*a* is pulled into the outer extrusion 46*a*, engages firmly against the inner wall of the outer extrusion 46*a*. This centers the inner extrusion within the outer extrusion while also defining the plurality of lumens 48*a*–48*d* around the circumference of the catheter as shown. The multiple lumens could thus be used for different purposes, if desired, but in a preferred embodiment they are all used to carry inflowing coolant liquid toward the end of the catheter. An important feature provided by this construction is that of assuring flow even if the catheter is bent to the point of creasing or kinking one side. Thus, if the catheter goes through a very tight bend and a kink develops at the lumen 48*c*, for example, the remaining lumens, or at least some of them will remain open and will continue delivering the necessary coolant liquid. It should be understood that the ridges 54 can be provided either on the outer surface of the inner extrusion 40*a* (as shown) or on the inner surface of the outer extrusion 46*a*. They could be provided on both surfaces if desired, in spaced and alternating relationship, although it is sufficient to provide them on one surface or the other.

Another feature of the construction shown in FIG. 4 is a series of inner protrusions 56 which serve to engage against and center the x-ray tube 38. These protrusions 56 could take different forms, but the tube 40*a* is an extrusion and thus they are typically continuous through the length of the tube 40*a*.

Figure 5:
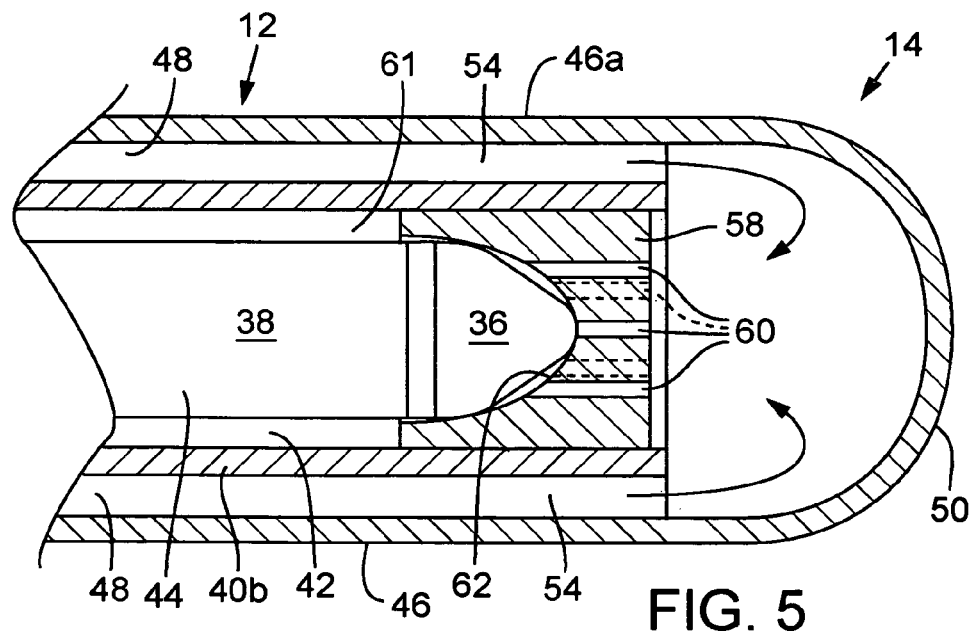
FIG. 5 is a schematic sectional view again showing the distal end of the catheter and indicating apparatus for distributing coolant over the anode end of an x-ray tube.

FIG. 5 shows a variation of the coolant flow arrangement shown in FIG. 4. Here, the outer tube 46*a* (which may be a capped extrusion) is essentially as shown in FIGS. 3 and 4, and the x-ray tube 38 is shown within the inner tube 40b but in this embodiment a coolant delivery head or "shower head" 58 is fitted into the end of the inner extrusion 40b as shown. Liquid coolant flowing through the annular flow space or lumen 48 (which may or may not be divided as in FIG. 4), reverses direction at the closed distal end 50 of the outer tube and enters the coolant delivery head 58 for distribution over the surface of the anode end 36 of the x-ray tube. A series of small orifices 60 are provided in the coolant distribution head 58, extending generally in the longitudinal direction of the catheter. These small orifices create a back pressure behind the distribution head 58, causing an accelerated flow as the liquid exits these orifices to flow over the anode end 36 and to a coolant return space 61. The downstream end 62 of the distribution head may be shaped somewhat like the exterior of the anode end 36, with space between the orifices and the anode end 36. The orifices are clear of the anode end, and should be spaced away by roughly about three times the orifice diameter (FIG. 5 is not precise or to scale). Preferably the coolant delivery head or distribution head 58 grips the x-ray tube 38 near the base of the anode end as shown, centering the x-ray tube within the inner extrusion 40b.

Figure 6:
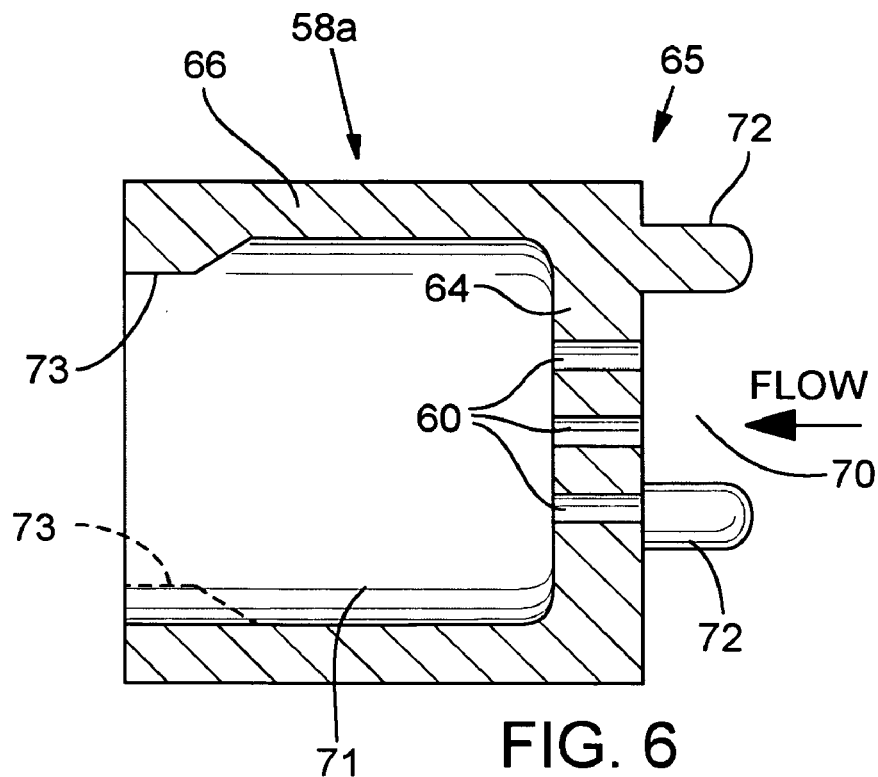
FIGS. 6 and 7 are longitudinal and transverse cross sectional and elevational views showing a component of the system of FIG. 4.
Figure 7:
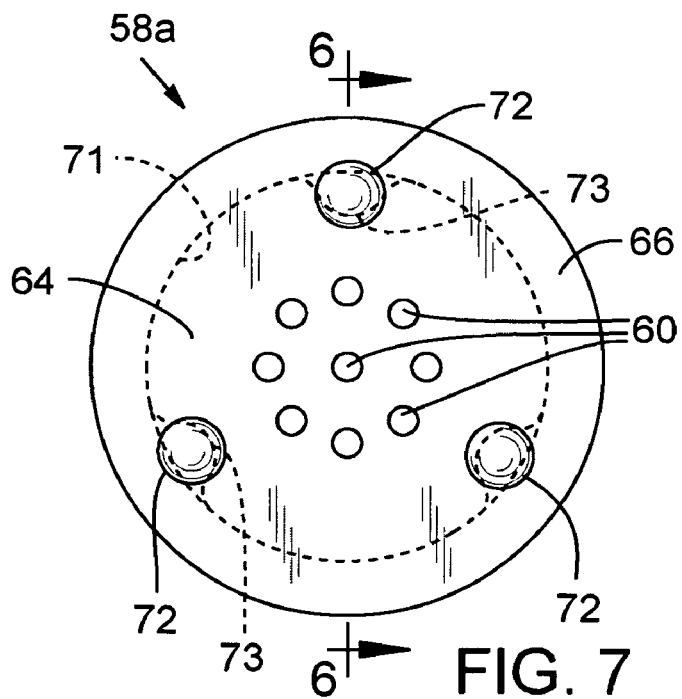

FIGS. 6 and 7 also show this "shower head" or liquid distribution head 58a in a somewhat different form. In FIGS. 6 and 7 the distribution head 58a is shown as a wall 64 with orifices 60, and a distal portion 65 in the distal direction of the wall and a proximal portion 66 proximal with respect to the wall 64. The distal portion 65 forms a chamber or area 70 into which the coolant liquid flows from the flow lumen 48 shown in FIG. 5 (after reversing direction), and it defines a coolant exit area 71 downstream of the orifices 60. Preferably a series of centering prongs 72 are included on this distal end for engaging against the end of the cooling tube 46a to retain and center the x-ray tube and the shower head 58a in place in the tube, allowing for distribution of coolant. FIG. 7 shows the coolant distribution head 58a in end view, showing the centering projections 72 and orifices 60. Relatively few orifices 60 are shown in these drawings; preferably there are at least three, more if needed for uniformity. The orifices need to be sized to create appropriate impedance to produce the back pressure discussed above. FIGS. 6 and 7 also show centering tabs or bumps 73 at the proximal end of the coolant distribution head 58a, to engage with and grip over and center the x-ray tube 38 in the distribution head 58a.

A filter preferably is included in the coolant liquid flow path to prevent clogging at the small orifices 60. The filter may be in the space 70 (FIG. 6), or it may be upstream in the flow path, outside the catheter and outside the human body.

Returning to FIG. 5, the configuration of showerhead 58 shown there allows longitudinal adjustment of the x-ray tube 38 within the catheter 12. The coolant distribution head 58 is secured firmly to the x-ray tube 38, but is slidable within the inner extrusion 40b. The inner surface of the inner extrusion 40b creates relatively low friction with the surface of the "shower head" 58, providing for the ability to slide the x-ray tube 38, its attached cable and the "shower head" 58 as a unit. The advantage of this is that the x-ray radiation can be moved to different positions in the vessel or other lumen as the treatment progresses, without moving the catheter itself. This can be important in cases where catheter movement may adversely affect tissue or adversely affect catheter position control.

FIGS. 8 and 9 also show this feature, whereby the position of the x-ray tube can be shifted during treatment. FIG. 8 shows a pull back box 76 which provides a means to pull the cable and x-ray tube back with respect to the inner and outer extrusions Depth indicators can be applied to the catheter shaft 77 and made visible to the user so that a depth reading can be made against structure 78 which is at the exterior of the patient.

FIG. 9 shows another embodiment of an applicator end in detail. The x-ray tube 38 is seen near the distal end. A tip 80 preferably is included at the end of the applicator for receiving and following a guide wire 82. In this form of applicator, the applicator end 84 has a balloon 85 as its outer surface. This balloon extends an appropriate distance to allow x-ray source positional movement as desired, longitudinally relative to the catheter 12a. The diameter of the assembly during use is reduced at 86 as shown in the drawing, where the construction may be as described above, inner and outer extrusions defining flow spaces for inflow and outflow or return of coolant liquid. The control and HV cable for the x-ray tube 38 is shown at 44. FIGS. 10 and 11 are cross sections of the construction shown in FIG. 9, as seen along the line 10—10 and 11—11 in FIG. 9, respectively. In FIG. 10 a coolant flow configuration is shown different from that described above, comprising a single extrusion 88 which has inflow lumens 90, at four different positions in the example shown in FIG. 10. The outflow is through spaces or lumens 92 which surround the central shaft 44 indicated in dashed lines, these return flow spaces being in recesses or grooves formed in the extrusion, as shown.

As shown in FIG. 11, the configuration is different closer to the x-ray tube 38, where the balloon 85 is included. Here, the balloon 85 forms not only the outer wall of the applicator, but forms the inflow lumen 96 in this region, between the balloon and the outer surface of an extrusion 98. This extrusion 98 may be formed as shown, with internally extending ridges 99 which engage firmly against the outside surface of the x-ray source 38. The outflow lumens are shown at 92a in this region. Downstream of the source, i.e. the x-ray tube 38, the situation is different and the outflow lumens 92a merge into a single space surrounding the control cable shaft 44, which is smaller in diameter than the radiation source 38. This return flow or outflow space is sealed to the proximal extrusion 88 such that the outflow space within the extrusion 98 connects directly and in sealed relationship with the outflow channels 92 in the proximal extrusion 88. At this point, i.e. the position 86 shown in FIG. 9, the inflow lumens 90 are sealed off, and radial openings are provided to communicate this space with the space 96 within the balloon 85.

In one sealing method, the extrusion 98 is butt-jointed to the extrusion 88 such that the flow space 92a is connected to the flow space 92 and sealed off from the inflow channels 90. The balloon 85 extends proximal to the above joint and makes connections with the inflow channels 90. The distal portion of the balloon 85 makes connections to the flow space 92a through punched holes on the wall of the extrusion 98.

The use of the external balloon space as the inflow channel also permits the function of a balloon at the applicator, i.e. this balloon 85 will expand under the pressure required to deliver the coolant through the system, and it will center the source within the body vessel or lumen. For this purpose the inlet pressure depends on the size of the balloon (smaller balloons typically require higher pressure) and its intended service. Generally, higher pressures can be achieved by applying more flow impedance to the inflow channels. Outflow pressure through the proximal extrusion 88 can be about ⅓ or ¼ inflow pressure, for purposes of proper function and safety.

Marker bands are shown at 99 in FIG. 9. These can be radiopaque metal or ink rings for the assistance of locating the x-ray source with respect to the treatment sites under fluoroscopy.

Figure 12:
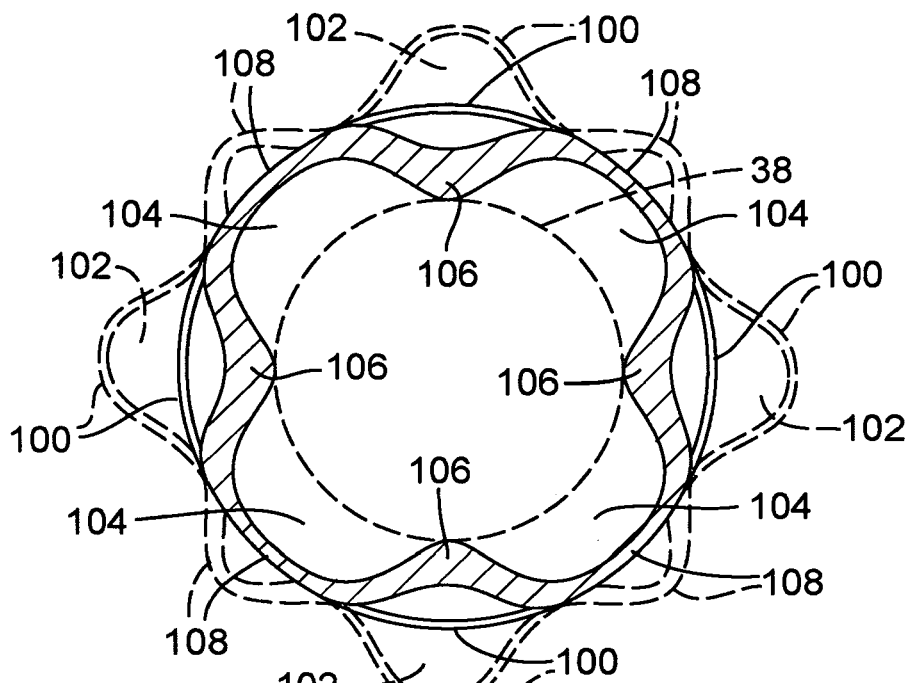
FIGS. 12 and 13 are transverse cross sectional views showing additional catheter extrusions for providing inflow and outflow/return channels, and also for providing expansible balloon sections at the exterior of the catheter.
Figure 13:
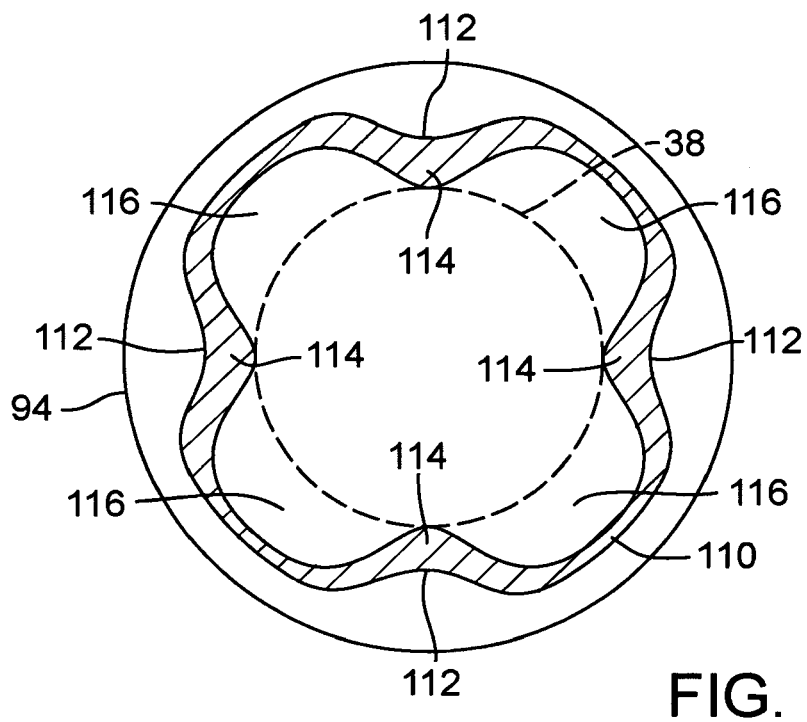

FIGS. 12 and 13 show cross sections of further embodiments of applicator extrusions to surround the x-ray source 38 while providing an expandable balloon feature for centering. In FIG. 12, at the distal end of the catheter, instead of adding an external balloon over an extrusion, the extrusion itself is formed with thin lumen walls 100 in a plurality of locations as shown, preferably at least three, for centering purposes. Under desired pressure of the coolant flow, the lumens 102 defined under the thin walls 100 will expand as balloon structures to provide more flow space. The expanded shape of each thin wall 100 is shown in dashed lines in the drawing. In this way, the size of the catheter, particularly the applicator end, upon insertion to a blood vessel or other body lumen can be maintained small, by providing little or no inflow coolant space. When the coolant is delivered under pressure through the catheter, however, the lumens 102 expand generally as indicated, providing the dual functions of adequate flow space for inflowing coolant and centering of the x-ray source 38 within the vessel or body lumen.

As in the construction described above, outflow or return for the coolant is provided between the extrusion 101 and the exterior of the radiation source 38 (or, proximal of the source, between the exterior of the HV/control cable and the interior of this extrusion 101). This can be divided into a plurality of return flow spaces 104, as shown in the drawing, by undulations or ridges 106 extending radially inwardly on the inner surface of the extrusion 101. These engage the exterior surface of the radiation source 38 and, as above, maintain the source 38 in a centered position. If desired for initial compactness of the extrusion 101, the return lumens 104 can also have a thin exterior wall 108, as shown. This provides for expansion of the walls 108 to expand the return flow lumens 104 to an adequate size for efficient flow during use of the catheter and applicator. Expansion of the lumens 104 under pressure as conditions, as with expansion of the lumens 102, enables the initial un-pressurized size of the applicator to be smaller. It is also possible to apply a vacuum to the lumens 102 and 104 of the applicator during insertion of the device, so that the size of the applicator/catheter is even more compact during insertion, while still providing ample flow space for coolant during operation.

Since the overall diameter of the applicator extrusion 101 may be on the order of about 2 mm, care must be taken in extruding this structure and the thin walls involved, particularly with respect to burst pressure.

FIG. 13 shows another configuration for the applicator end of the catheter, providing inflow and outflow lumens for coolant. As in FIG. 11, an external balloon 94 is attached to surround an extrusion 110. In this form, however, to reduce catheter size the distal extrusion 110 can be shaped as shown. Note that the extrusion 110 is not circular, but is flat or even grooved inwardly at a series of locations, preferably three or four or more, as shown at 112 in FIG. 13. These locations 112 are at the same angular positions as bumps or ridges 114 formed on the inner side of the extrusion, these ridges 114 engaging against the outside surface of the radiation source 38 as in above described embodiments. The balloon 94 is sealed to the exterior of the extrusion 112 at the distal end, and is sealed to an adjacent proximal extrusion near the proximal end, in the same manner as in FIG. 9.

When the catheter is inserted into a vessel or lumen of the patient, the user applies a vacuum to the inlet and outlet ports of the cooling system, at the proximal end of the catheter. This not only maintains the balloon 94 tight against the outside of the extrusion 110, but also pulls the outflow/return lumens 116 inwardly, into contact with or nearly into contact with the radiation source 38, considerably reducing the size of the applicator at the distal end of the catheter. As above, when the coolant is introduced under pressure, this will dilate the lumens, both inflow and outflow, to the flow area needed.

Figure 14:
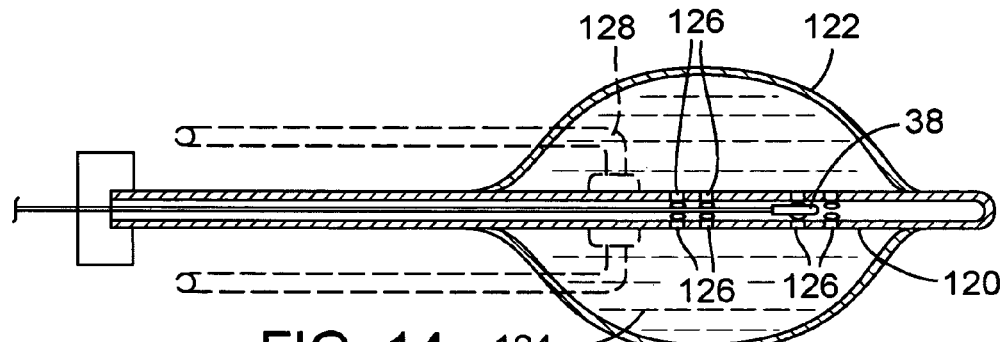
FIGS. 14–16 schematically illustrate arrangements wherein a balloon or applicator contains coolant liquid for the x-ray source, either as a static coolant or a flowing coolant.
Figure 15:
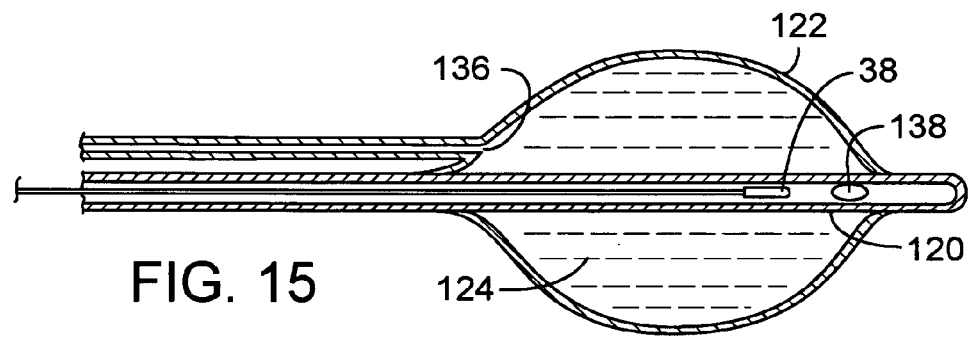
Figure 16:
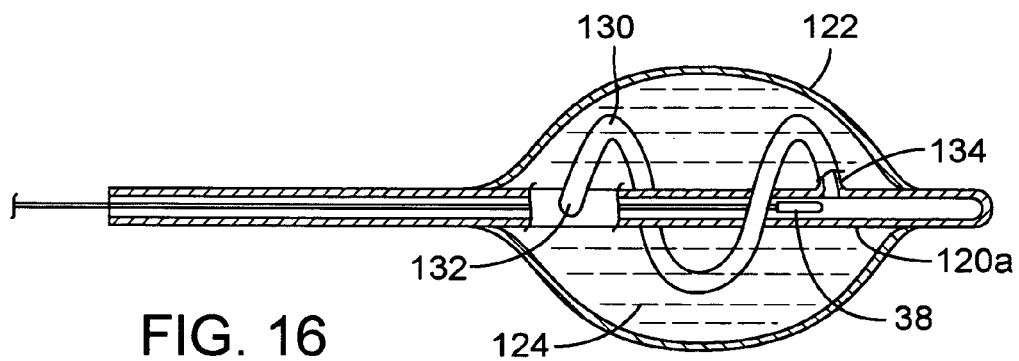

Further embodiments of the invention, wherein an applicator balloon of the system has an inflation liquid which itself serves as coolant liquid, are shown in FIGS. 14–16. These drawings show the distal end of the catheter 12, and in each case an x-ray source 38 is contained within the central guide 120 of the catheter near the distal end, with an inflatable applicator balloon 122, used for positioning, surrounding the central guide 120 in the region of the radiation source 38. In each case the applicator 122 is shown inflated, and the inflation liquid 124 within the applicator is used as a coolant for the x-ray tube 38, either statically or with flow of the coolant liquid.

One embodiment is shown in FIG. 14. Here, the saline or other liquid 124 that fills the applicator cools the x-ray source 38 without any movement of the liquid. The central guide 120 has holes, indicated at 126, to allow communication between the fluid filled applicator balloon 124 and the interior of the central guide 120. A natural convection will be established to circulate the cooling liquid. A variation of this embodiment is shown with the addition of a heat exchanger 128 in dashed lines. The heat exchange is shown only schematically, with a series of cooling coils inside the applicator balloon and with the heat exchanger tube penetrating the walls of the balloon. In practice the lumens delivering and returning the heat exchanger coolant liquid through the exchanger 128 will be incorporated in the catheter and can be formed in one of the ways as described above. Although the device of FIG. 14 is generally designed for short treatment times, allowing the cooling system more simplicity, the use of a heat exchanger to draw withdraw heat increases the versatility of the device. With the heat exchanger the coolant liquid does not come into contact with either the x-ray source or the applicator fluid 124 thus avoiding the need for sterile cooling fluid and avoiding further complications in the safe design of a medical device. In either event, a pressure regulator system may be employed to maintain the pressure in the applicator balloon at a desired value in the presence of increasing temperature and possible gas buildup (steam).

A variation of the static cooling system shown in FIG. 14 is depicted in FIG. 16. Here, a heat exchanger is again included but comprises a thin walled tubing 130 that passes though the interior volume of the applicator 122 and in connected to inlet and outlet ports 132 and 134 on the applicator neck or central guide 120a. The coolant controller 18 (FIGS. 1 and 2) can provide cooling liquid that transfers heat from the applicator liquid to the controller liquid, in a heat exchange relationship, thus removing heat from the applicator. Although FIG. 16 is schematic, it indicates that flow channels for the heat exchanger coolant liquid are contained within the central applicator shaft or neck 120a of the catheter. The advantage for this approach is that the impedance of the liquid coolant flow is very low, and the pressure necessary to pump the required flow rate to the applicator is very low. Again this avoids the need for sterile cooling fluid. Also, the illustrated cooling arrangement used at a low flow rate will slow down the rate of heat buildup in the applicator balloon, thus relying partially or principally on the static cooling effect of the liquid in the balloon. This approach allows higher power x-ray sources to be operated with less complicated cooling systems, as compared to small-lumen catheter based cooling.

FIG. 15 schematically shows another system utilizing the applicator inflation liquid 124 as a coolant, but in this case in an active flow cooling system. The coolant/inflation liquid can be pumped into the applicator while maintaining a differential pressure sufficient to maintain the desired expansion of the applicator 122. Internal guides within the application (not shown) can direct the incoming coolant liquid over the x-ray source and then remove the liquid from a convenient location along the central guide 120. FIG. 15 shows a liquid inlet 136 into the applicator balloon, and a hole 138 in the central guide tube which communicates the liquid 124 from the applicator 122 into the central guide. Cooling liquid outflow in the return direction is through the central guide. Note that the inlet 136 may also be incorporated into the central/applicator neck 120.

As an example, for the smallest applicator envisioned for a breast therapy device, with a 3 cm diameter applicator balloon, the fill volume would be approximately 15 cm$^3$. For a 5 watt x-ray source operating for five minutes, the temperature rise would be approximately 25° C. For fluids cooled to near 0° C., the final temperature would be below body temperature, and for fluids starting at near 10° C., the final temperature would be near body temperature of 37° C. In embodiments where there is no active flowing liquid to cool the x-ray source and the source anode temperature can be very high, convection can be used to move the cooling liquid without resorting to pumps or other mechanical solutions. Part of the x-ray source guide 120 can position the x-ray source away from the walls of the guide tube, and with openings in the guide tube proximal to the source and an open end distal to the source, strong convection can be caused to occur and used to continually move new coolant liquid over the source.

As temperature rises in the applicator, the pressure in the applicator will also rise. A bladder (not shown) that expands with increasing pressure can be used to compensate for the increasing pressure. This is preferably located outside the human body in the coolant path in series with the balloon. This design takes into account the elastic expansion of the applicator and the bladder. When the applicator balloon reaches a specific size, the amount of further expansion for increasing pressure is limited. Additional pressure expands into the bladder. An alternative approach is to have a drain tube and a pressure relief valve that opens when the pressure exceeds a specific value. The drain tube can comprise a lumen in the central guide 120 of the catheter.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A cooling system for a miniature x-ray tube capable of being delivered in a catheter to a desired location in a lumen of the human body, comprising:

a catheter having multiple lumens for carrying a liquid coolant, with the x-ray tube contained in a distal end of the catheter, the x-ray tube having an anode end near the distal end of the catheter, the catheter including a coolant delivery head distal relative to the anode, for receiving coolant from at least one inflow lumen of the catheter and for delivering a distributed flow of coolant liquid over the anode end of the x-ray tube, the delivery head having a coolant entry end fluidly connected to said inflow lumen and having a wall with a series of orifices for delivery of the coolant liquid toward a proximal direction of the catheter, toward and over said anode end, the orifices being spaced apart and distributed in position so as to spread the coolant liquid over substantially the entire area of the anode end so as efficiently to cool the anode, and a coolant return space around the x-ray tube for collecting coolant liquid that has flowed over the anode, said return space being connected to an outflow lumen in the catheter for returning the coolant liquid through the catheter toward a proximal end of the catheter and out of a human body.

2. The cooling system of claim 1, further including a coolant reservoir tank connected to said proximal end of the catheter, for receiving coolant liquid returning from the x-ray tube, and a pump for delivering coolant liquid through said inflow lumen of the catheter.

3. The cooling system of claim 1, wherein the coolant delivery head is generally cylindrical and has a proximal axial end that overlaps and essentially envelops the anode end of the x-ray tube.

4. The cooling system of claim 1, wherein the coolant delivery head comprises a generally cylindrical body having two axial ends, a distal end distal of said wall and a proximal end proximal of said wall, the proximal end having centering tabs extending radially inwardly to grip the exterior of the x-ray tube and effective to center the x-ray tube within the catheter, the distal end forming said coolant entry space.

5. The cooling system of claim 1, further including a filter in a path of the coolant liquid upstream of said orifices, the filter being effective to filter out particles that could plug the orifices in the coolant delivery head.

6. The cooling system of claim 5, wherein the filter is located within the coolant delivery head.

7. The cooling system of claim 1, wherein the coolant liquid includes a surfactant suitable for reducing surface tension of the coolant liquid and for improving heat transfer.

8. The apparatus cooling system of claim 1, wherein the coolant liquid is degassed to eliminate bubbles.

9. The apparatus cooling system of claim 1, wherein the catheter comprises two concentric extrusions, including an outer extrusion and an inner extrusion, the inner extrusion having radially inwardly extending ridges on its interior, positioned and sized to engage an exterior surface of the miniature x-ray tube, and one of the inner and outer extrusions having, on its surface facing toward the other, stand-off ridges that engage the surface of said other extrusion, forming between the inner and outer extrusions at least one coolant flow channel, serving as said inflow lumen of the catheter for inflow of coolant liquid toward the coolant delivery head.

10. The cooling system of claim 9, wherein the ridges extending between the inner surface of the outer extrusion and the outer surface of the inner extrusion are substantially continuous through the catheter, forming a plurality of fluid flow lumens through which coolant liquid flows toward the coolant delivery head, the plurality of lumens thus distributing the flow of inflowing coolant liquid around the circumference of the catheter such that in the event of a relatively sharp bend in the catheter, causing one inflow lumen to collapse, at least one other inflow lumens are available to assure continued flow.

11. The cooling system of claim 10, wherein the space between the outer extrusion and the inner extrusion forms at least three separate channels around the circumference of the catheter for inflowing coolant liquid.

12. The cooling system of claim 9, wherein the inner and outer extrusions are formed of thermoplastic or thermoset material.

13. The cooling system of claim 1, wherein the coolant liquid flows into the catheter at a temperature in the range of about 0° C. to about 37° C.

14. The apparatus cooling system of claim 13, wherein the coolant flows into and back out of the catheter at a rate of less than about 150 cc per minute.

15. The cooling system of claim 1, wherein the catheter includes a flexible, extendable wall portion in an area of the catheter near the x-ray tube, said extendable wall portion having behind it a chamber in communication with said inflow lumen of the catheter through which coolant liquid flows en route to cool the x-ray tube, such that when the catheter is in place in the human body the coolant liquid can be pressurized so as to cause the extendable portion of the catheter wall to extend outwardly to engage tissue of the body lumen and thus to center the x-ray tube.

16. The cooling system of claim 1, wherein the x-ray tube is translatable axially within the catheter, in fore/aft direction, for adjusting the position of the x-ray tube in the body lumen without moving the catheter.

17. The cooling system of claim 1, including a temperature monitor positioned to monitor temperature of coolant liquid flowing out of the catheter, to verify flow of coolant over the x-ray tube.

18. The cooling system of claim 1, further including a temperature monitor positioned to monitor temperature of coolant liquid flowing into the catheter.

19. The cooling system of claim 1, wherein said inflow lumen of the catheter within which coolant fluid flows toward the x-ray tube is in an outer portion of the catheter, said outflow lumen being at an inner portion of the catheter, said inflow lumen having a flexible outer wall whereby a vacuum can be applied to the inflow lumen while the catheter is implanted, to shrink the diameter of the catheter, then the catheter can be re-expanded when coolant liquid is pumped through the catheter.

20. The cooling system of claim 18, including an outer extrusion surrounding an inner extrusion and forming an annular space between the lumens, the space being divided around its circumference into multiple said inflow lumens.

21. The cooling system of claim 1, further including pressure monitors in the inflow and outflow lumens of the catheter, for confirming the continued flow of coolant liquid.

22. The cooling system of claim 1, further including a coolant liquid reservoir connected to the inflow and outflow lumens of the catheter, and including a peristaltic pump for pumping coolant liquid through the catheter without contamination.

23. A cooling system for a miniature x-ray tube capable of being delivered in a catheter to a desired location in a lumen of the human body, comprising:
   a catheter having multiple lumens for carrying a liquid coolant, with the x-ray tube contained in a distal end of the catheter,
   the x-ray tube having an anode end near the distal end of the catheter,
   an inflatable balloon near the distal end of the catheter, sealed to the catheter and expandable outwardly from the catheter for positioning of the catheter and x-ray tube, and including a liquid flow channel comprising one of said multiple lumens and carrying inflowing coolant liquid, the flow channel communicating with the applicator balloon to inflate the applicator balloon with coolant liquid,
   the liquid flow channel continuing from the applicator balloon to flow the liquid over the anode end of the x-ray tube, and including an outflow channel comprising another one of said multiple lumens, positioned to carry liquid that has flowed over the anode end in a return direction out of the human body, and
   including pressure regulator means for maintaining a desired pressure in the applicator balloon while allowing coolant liquid to flow through the applicator balloon and over the anode end of the x-ray tube.

24. The cooling system of claim 1, wherein the inflow lumen is in an outer portion of the catheter, and wherein the catheter has an outer wall forming an outer boundary of the inflow lumen, the outer wall being formed of low thermally conductive material so as to serve as an insulator to minimize heating of the coolant as it flows through the catheter and through the human body toward the x-ray tube.

25. A cooling system for a miniature x-ray tube capable of being delivered in a catheter to a desired location in a lumen of the human body, comprising:
   a catheter having multiple lumens for carrying a liquid coolant, with the x-ray tube contained in a distal end of the catheter,
   the x-ray tube having an anode end near the distal end of the catheter, and
   at least two of the lumens of the catheter being generally coaxial and concentric, including an outer lumen serving as an inflow lumen for coolant liquid and having a closed distal end and an inner lumen serving as an outflow or return lumen for coolant liquid, the x-ray tube being positioned centrally and generally coaxially with respect to the inner lumen and positioned such that coolant liquid from the inflow lumen flows over the anode end of the x-ray tube, and returns in the proximal direction of the catheter through the inner outflow lumen.

26. The cooling system of claim 25, further including a coolant reservoir tank connected to said proximal end of the catheter, for receiving coolant liquid returning from the x-ray tube, and a pump for delivering coolant liquid through said inflow lumen of the catheter.

27. The cooling system of claim 25, wherein the coolant liquid includes a surfactant suitable for reducing surface tension of the coolant liquid and for improving heat transfer.

28. The cooling system of claim 25, wherein the coolant liquid is degassed to eliminate bubbles.

29. The cooling system of claim 25, wherein the catheter comprises two concentric extrusions, including an outer extrusion and an inner extrusion, the inner extrusion having radially inwardly extending ridges on its interior, positioned and sized to engage an exterior surface of the miniature x-ray tube, and one of the inner and outer extrusions having, on its surface facing toward the other, stand-off ridges that engage the surface of said other extrusion, forming between the inner and outer extrusions at least one coolant flow channel, serving as said inflow lumen of the catheter for inflow of coolant liquid.

30. The cooling system of claim 29, wherein the ridges extending between the inner surface of the outer extrusion and the outer surface of the inner extrusion are substantially continuous through the catheter, forming a plurality of fluid flow lumens through which coolant liquid flows toward the coolant delivery head, the plurality of lumens thus distributing the flow of inflowing coolant liquid around the circumference of the catheter such that in the event of a relatively sharp bend in the catheter, causing one inflow lumen to collapse, at least one other inflow lumen is available to assure continued flow.

31. The cooling system of claim 30, wherein the space between the outer extrusion and the inner extrusion forms four separate channels around the circumference of the catheter for inflowing coolant liquid.

32. The cooling system of claim 25, wherein the coolant liquid flows into the catheter at a temperature in the range of about 0° to 37° C.

33. The cooling system of claim 32, wherein the coolant flows into and back out of the catheter at a rate of less than about 150 cc per minute.

34. The cooling system of claim 25, wherein the catheter includes a flexible, extendable exterior wall portion in an area of the catheter near the x-ray tube, said extendable wall portion having behind it a chamber in communication with said inflow lumen of the catheter through which coolant liquid flows en route to cool the x-ray tube, such that when the catheter is in place in the human body the coolant liquid can be pressurized so as to cause the extendable portion of the catheter wall to extend radically outwardly to engage tissue of the body lumen and thus to generally center the x-ray tube.

35. The cooling system of claim 25, wherein the x-ray tube is translatable axially within the catheter, in fore/aft direction, for adjusting the position of the x-ray tube in the body lumen without moving the catheter relative to the human body.

36. The cooling system of claim 25, including temperature monitors positioned to monitor temperature of coolant liquid flowing out of the catheter, to verify flow of coolant over the x-ray tube.

37. The cooling system of claim 25, wherein said inflow lumen of the catheter within which coolant fluid flows toward the x-ray tube is in an outer portion of the catheter, said outflow lumen being at an inner portion of the catheter, said inflow lumen having a flexible partially collapsible outer wall such that a vacuum can be applied to the inflow lumen while the catheter is implanted, to shrink the diameter of the catheter, then the catheter can be re-expanded when coolant liquid is pumped through the catheter.

38. The cooling system of claim 37, including an outer extrusion surrounding an inner extrusion and forming an annular space between the lumens, the space being divided around its circumference into multiple said inflow lumens.

39. The cooling system of claim 25, further including pressure monitors in the inflow and outflow lumens of the catheter, for confirming the continued flow of coolant liquid.

40. The cooling system of claim 25, further including a coolant liquid reservoir connected to the inflow and outflow lumens of the catheter, and including a peristaltic pump for pumping coolant liquid through the catheter without contamination.

41. The cooling system of claim 25, wherein the inflow lumen is in an outer portion of the catheter, and wherein the catheter has an outer wall forming an outer boundary of the inflow lumen, the outer wall being formed of low thermally conductive material so as to serve as an insulator to minimize heating of the coolant as it flows through the catheter and through the human body toward the x-ray tube.

42. The cooling system of claim 25, further including an inflatable applicator balloon near the distal end of the catheter, sealed to the catheter and expandable outwardly from the catheter for positioning of the catheter and x-ray tube, and including a liquid flow channel from said outer lumen into the applicator balloon, to inflate the applicator balloon with coolant liquid, and a return flow channel from the applicator balloon through the catheter to said inner lumen, for flow of coolant liquid from the applicator balloon into the inner lumen and over the anode end of the x-ray tube, and including pressure regulator means for maintaining a desired pressure in the applicator balloon while allowing coolant liquid to flow through the applicator balloon and over the anode end of the x-ray tube.

43. A cooling system for a miniature x-ray tube capable of being delivered in a catheter to a desired location in a lumen of the human body, comprising:
  a catheter having at least one lumen for carrying a coolant liquid, with the x-ray tube contained in a distal end of the catheter,
  the x-ray tube having an anode end near the distal end of the catheter,
  an applicator balloon connected to the catheter near the distal end of the catheter, the balloon being expandable out from the catheter when inflated by a fluid,
  the catheter including a flow channel connecting said at least one lumen to the interior of the applicator balloon, and
  fluid communication means in the catheter for providing fluid communication between liquid in the applicator balloon when inflated and the anode end of the x-ray tube, for static cooling of the x-ray tube by the coolant liquid which also inflates the applicator balloon.

44. The cooling system of claim 43, wherein the fluid communication means is arranged to provide for convection of liquid coolant when the anode is heated during use, so that cooling liquid continually flows over the anode end.

45. The cooling system of claim 43, further including a heat exchanger tube within the applicator balloon, connected to an inflow and outflow conduit whereby liquid coolant can be circulated through the heat exchanger tube to withdraw heat from the liquid in the applicator balloon with low flow impedance.

* * * * *